United States Patent [19]

Stacey et al.

[11] Patent Number: 4,983,519

[45] Date of Patent: Jan. 8, 1991

[54] RECOMBINANT DNA CLONES OF ESSENTIAL NODULATION GENES OF BRADYRHIZOBIUM JAPONICUM

[76] Inventors: Gary Stacey, 2304 Sutters Mill La.; Maria G. Schell, 1903 Sutters Mill La., both of Knoxville, Tenn. 37923; Anthony J. Nieuwkoop, 390 Mayfair St., Holland, Mich. 49424; Nirupama A. Deshmane, 1611 Laurel Ave., Knoxville, Tenn. 37916; Zsofia Banfalvi, H-6723, Szeged, Vajda u. 18/B, Hungary

[21] Appl. No.: 77,561

[22] Filed: Jul. 24, 1987

[51] Int. Cl.$^5$ .................... C12N 15/00; C12N 1/00; C12R 1/41; C07H 15/12

[52] U.S. Cl. ...................... 435/172.3; 435/252.2; 435/252.3; 435/320; 435/878; 536/27; 935/11; 935/72

[58] Field of Search .................... 536/27; 71/7; 435/172.3, 252.2, 252.3, 320

[56] References Cited

PUBLICATIONS

Long et al., 1982, Nature, 298:485.
Banfalvi et al., 1983, Mol. Gen. Genet., 203:42.
Downie et al., 1983, Embo J., 2:947.
Schofield et al., 1984, Plant Mol. Biol., 3:3.
Russell et al., 1985, J. Bacteriol., 164:1301.
Lamb et al., 1986, Mol. Gen. Genet., 202:512.
Noti et al., 1985, Proc. Natl. Acad. Sci. USA, 82:7379.
Marvel et al., 1985, Proc. Natl. Acad. Sci. USA, 82:5841.
Scott, 1986, Nucl Acids Res., 14:2905.
Jacobs et al., 1985, J. Bacteriol., 162:469.
Rosen et al., 1984, Nucl. Acids Res., 12:9492.
Torpol et al., 1984, Nucl Acids Res., 12:9509.
Scott et al., 1985, Mol. Gen. Genet., 201:43.
Mulligan et al., 1985, Proc. Natl. Acad. Sci., 82:6609.
Innes et al., 1985, Mol. Gen. Genet., 201:426.
Rossen et al., 1985, Embo J., 4:3369.
Peters et al., 1986, Science, 223:977.
Redmond et al., 1986, Nature, 323:632.
Aronson et al., Microbiol. Rev., Mar. 1986, pp. 1-24.
Vaeck et al., Nature, 1987, 328:33-37.
Mol. Gen. Genet., 207:15 So et al., 1987.
J. Bacteriol., 169:2631, Nieuwkoop et al., 1987.
Noti et al., 1986, J. Bacteriol., 167(3): 744-783.
Lamb et al., 1986, pp. 79-86, Dri NATO ASI Ser., Ser. H, 4 (Recognit. Microbe-Plant Symbiotic Pathog. Interact.).

Primary Examiner—Charles F. Warren
Assistant Examiner—David T. Fox
Attorney, Agent, or Firm—Foley & Lardner

[57] ABSTRACT

Recombinant DNA clones according to the invention contain nodABCDIJL genes of B. japonicum. These clones can be used to practice a method wherein a nod− strain of Rhizobium or Bradyrhizobium bacteria lacking one or more of these genes is converted to a nod+ strain by transfering one or more of the missing genes to the strain. According to a further aspect of the invention, nucleotide sequences have been identified which control the expression of nod LABC genes of Bradyrhizobium japonicum in the presence of flavones produced by the plant roots. By linking such sequences with a gene having a desired characteristic, such as a gene encoding for production of a plant parasite toxin, bacterial can be created which selectively express the characteristic only in the presence of the flavone which triggers expression of the gene.

3 Claims, 3 Drawing Sheets

```
                                       Nod D
                     20            .   40  ⤸  .   60            .   80
5' --GCGTCGAGCGCAACGAGAAGATTTAGATCAAGTCCCTTGAACCGCATGTGATGAGTCTATCCATCGTGTGGATGTGTTCT
        A  D  L  A  V  L  L  N  L  D  L  G  K  F  R  M

.   100           .   120           .   140           .   160
    ATCGAAACAATCGATTTTACCAAACTGGGGGAGGTTGGATAGCAAACTGAAGTTTGGAAAAAGCAATTAGACGCGCCACG
              ─────────────
               consensus .   180           .   200           .   220           .   240
    ATGGTTTCCGGTCGTTC ACGTG GCTAAGA AAGAGCTCCCAGAC TGGCGAGGCACCATGGCGC  GTT T TGTTTCTC ORF 1
                 .   260           .   280           . 300            .   320
    CTTAAGCGTGGCCGTTCGAACGCCAAGCGCGTCCCGATAAACGTTGGTATGCAGATATCATCCGTTTCCATATTTCAGGT
                                          ─────       M  Q  I  S  S  V  S  I  F  Q  V .   340           .   360           .   380           .   400
    TTACCCGCGTACAATTGAGGGCGCGTTCAGCCTCATTCTAGTGTCGAAGAATAGAGGCAGACGCAGGTTGCGGATGCCAA
     Y  P  R  T  I  E  G  A  F  S  L  I  L  V  S  K  N  R  G  R  R  R  L  R  M  P .   420           .   440           .   460           .   480
    GAATTCCAGGCGCCGTTCCAAATGGCTCGCCTGTCCAGTGCATGTGGGGCGTGTCGAAGATGTATAAAAGCCAGTGTGAT
     R  I  P  G  A  V  P  N  G  S  P  V  Q  C  M  W  G  V  S  K  M  Y  K  S  Q  C  D .   500           .   520           .   540           .   560
    CTGATGCCGCTCCGATGCGCCATCGATGAGGCTTGCGCGCCGATGGCCGGCCCTCAGACGTCAAAGCGCCGGAGGCATGC
     L  M  P  L  R  C  A  I  D  E  A  C  A  P  M  A  G  P  Q  T  S  K  R  R  R  H  A .   580           .   600           .   620           .   640
    GACTGCAGGCACAAAAGCTCGCTGGTGCAGACAGGTTCTGCTAGCCCAACCGCCTCGTCGGCAGCTTCCGAGTTATCGTG
     T  A  G  T  K  A  R  W  C  R  Q  V  L  L  A  Q  P  P  R  R  Q  L  P  S  Y  R .   660           .   680           .   700           .   720
    AGCGCGGCATCAACCGCACGAGGGTGCAATCAAGCGATCGCTCCGTCGCGCAAAGGCCAGCGCGCGAGTAGGCGAGCAGT
     E  R  G  I  N  R  T  R  V  Q  S  S  D  R  S  V  A  Q  R  P  A  R  E .   740           .   760           .   780           .   800
    GCCGAGCTCCGACAGAGCATGGCGCGCATCTCAGCATTCATCGGCGGTTCGGCGAATAGCGAATTGACGTGACCATCCCC Nod A
                 .   820           .   840           .   860           .   880
    GCTCTTCATTCCACCGGCGCAAGGAAGCTCGCCATGAACATTGCCGTCTCCCCGACTTGCGGAAGGATCTTCTGGGCGCG
                   ──                   M  N  I  A  V  S  P  T  C  G  R  I  F  W  A  R
                   SD .   900           .   920           .   940           .   960
    CTCAAGTGCAGTGGAGCCTTTCGTTGGGAAAGTGAACTGCAGCTCGACGATCATGCGAGCTCGCGATTCTTCTAAGAGTT
      S  S  A  V  E  P  F  V  G  K  V  N  C  S  S  T  I  M  R  A  R  D  S  S  K  S

ACGGACGACGGTCTTATCG-- 3'
     Y  G  R  R  S  Y

FIG 3
```

RECOMBINANT DNA CLONES OF ESSENTIAL NODULATION GENES OF *BRADYRHIZOBIUM JAPONICUM*

FIELD OF THE INVENTION

The present invention relates to bacterial genes involved in the nodulation of leguminous plants by species of Rhizobium and Bradyrhizobium. More particularly, this invention relates to recombinant DNA clones containing the nod LABCDIJ genes of *Bradyrhizobium japonicum* involved in the establishment of a $N_2$ fixing symbiosis between this bacteria and its host plant, oligodeoxyribonucleotides related to such genes, and methods for manipulating these genes to enhance the nodulation properties of rhizobia or even provide controlled expression of a foreign gene inserted by recombinant DNA techniques.

BACKGROUND OF THE INVENTION

Bacteria of the genera Rhizobium and Bradyrhizobium, collectively referred to as rhizobia, possess the ability to infect leguminous plants and establish a nitrogen-fixing symbiosis. This process is called nodulation and the morphological structure formed on the root in which the bacteria reside is termed a nodule. The formation of a nodule is a developmental process both from the standpoint of the bacteria and the plant. Each step in the process likely involves one or more bacterial and plant genes.

The genes in rhizobia (i.e., bacteria of the genera Rhizobium and Bradyrhizobium) involved in nodule formation and function are sometimes referred to as sym (for symbiotic) genes. The sym genes are further classified into three broad categories: nif, fix, and nod genes. The distinction between these genes is not always clear. For the purposes of this invention, nif genes include those that are responsible for production of the nitrogen-fixing enzyme, nitrogenase (i.e., nif KDH) and all other genes that are analogous to nif genes already identified in *Klebsiella pneumoniae*. The fix genes are those genes necessary for nitrogen fixation but which are not comparable to the nif genes of *K. pneumoniae*. The nod genes are those genes involved in the formation of the nodule.

Knowledge of the nodulation genetics of "fast-growing" Rhizobium species is relatively well advanced. The same cannot be said in relation to the nodulation genetics of "slow growing" Bradyrhizobium species, an example of which is *B. japonicum* whose primary host is soybean. The first nodulation genes isolated were genes from *R. meliloti* (host alfalfa) encoding the ability to induce curling of plant root hairs (Long et al., 1982, *Nature* 298:485; Banfalvi et al., 1983, *Mol. Gen. Genet.* 203:42; Downie et al., 1983, *EMBO J.* 2:947; Schofield et al., 1984, *Plant Mol. Biol.* 3:3. The appearance of curled root hairs is one of the first microscopic indications of successful infection by rhizobia. These genes have now been isolated from a number of Rhizobium species.

Nodulation genes of *B. japonicum* were approximately identified in Russell et al, 1985, *J. Bacteriol.* 164:1307. Russell et al. found an 11.7 kb region of homology with two Rhizobium species containing consecutive 5.6, 3.9 and 1.7 HindIII fragments. Russell et al. created a recombinant DNA clone, pRjUT10, containing this region among others. A 1.8 kb portion of the 3.9 kb fragment was found essential to nodulation as indicated by the presence or absence of root hair curling function, but no identification of specific nod genes was made. Lamb et al. (1986, *Mol. Gen. Genet.* 202:512) have disclosed approximate locations for nodABC genes of *B. japonicum*. The general location of these genes is also known for other Bradyrhizobium strains (Noti et al, 1985, *Proc. Natl. Acad. Sci. USA* 82:7379; Marvel et al, 1985, *Proc. Natl. Sci. USA* 82:5841; Scott, 1986, *Nucl. Acids. Res.* 14:2905.

In both Rhizobium and Bradyrhizobium, root hair curling genes are found clustered and consist of six genes i.e., nod ABCDIJ (Jacobs et al, 1985, *J. Bacteriol.* 162:469; Rossen et al, 1984, *Nucl. Acids Res.* 12:9492; Torpol et al, 1984, *Nucl. Acids Res.* 12:9509.) DNA-DNA hybridization and sequencing studies of the nodABCDIJ genes have demonstrated significant homology among different Rhizobium and Bradyrhizobium species. See, e.g. Scott et al, 1985, *Mol. Gen. Genet.* 201:43. Due to the broad conservation of these genes in a variety of species, this region is generally referred to as the "common" Nod locus.

The nodABCD region has been sequenced from only one Bradyrhizobium species, *B. parasponia* (Scott, 1986, *Nucl. Acids Res.* 14:2905.) Surprisingly, the DNA sequence reveals an additional gene upstream of the nodABC transcript. This gene has been termed nodK. In the present invention, the presence of an additional gene upstream of nodABC in *B. japonicum* is also disclosed. However, since the homology of the new *B. japonicum* gene to the nodK gene is less than 30%, the newly identified gene is unique and we have named it nodL. "Homology" refers generally to the extent to which the two genes contain DNA sequences in common.

In free-living culture, the nodABC genes of Rhizobium and Bradyrhizobium species are not transcribed at an appreciable level. However, in the presence of the host plant these genes are apparently induced and are essential for nodule formation. In three different Rhizobium species, *R. leguminosarum*, *R. meliloti*, and *R. trifolii*, the induction of nodABC transcription has been shown to be specifically induced by the presence of plant-produced phenolic compounds, flavones (Mulligan et al, 1985, *Proc. Natl. Acad. Sci.* 82:6609; Innes et al, 1985, *Mol. Gen. Genet.* 201:426; Rossen et al, 1985, *EMBO J.* 4:3369; Peters et al, 1986, *Science* 223:977; Redmond et al, 1986, *Nature* 323:632).

The present invention relates to the nodABCDIJ genes of *B. japonicum*, as well as the nodL gene described in the present invention, which have not been clearly characterized in the prior art, and a variety of products and methods that can be practiced using such genes.

SUMMARY OF THE INVENTION

Recombinant DNA clones according to the invention contain nodABCDIJL genes of *B. japonicum*. These clones can be used to practice a method of the invention wherein a nod− strain of Rhizobium or Bradyrhizobium bacteria lacking one or more of these genes is converted to a nod+ strain by transferring one or more of the missing genes to the strain by, for example, complementation.

According to a further aspect of the invention, nucleotide sequences have been identified which characterize the nodA, nodL, and nodD genes of *B. japonicum*, as well as the S-D sequences associated with nodL and nodA genes in *B. japonicum*, and a promoter DNA region disposed between the nodD and nodL genes.

According to another aspect of the invention, nucleotide sequences have been identified which control the expression of nodLABC genes of *Bradyrhizobium japonicum* in the presence of flavones produced by the plant roots. These sequences can be isolated as oligodeoxyribonucleotides. By linking such sequences with a foreign gene having a desired characteristic, such as a gene from another organism encoding for production of a plant parasite toxin, bacteria can be created which selectively express the characteristic only in the presence of the flavone which triggers expression of the gene. Such genetically engineered bacteria can be used according to a further method of the invention to protect plant roots from parasites. The toxin is produced by the bacteria only in the presence of the plant root where it is needed.

BRIEF DESCRIPTION OF THE DRAWING

In the accompanying drawing:

FIG. 3 is a diagram showing the complete nucleotide sequence of the promoter region of nodLABC and terminal, partial sequences for nodA and nodD. Amino acid sequences for the end of nodD, nodL, and the start of nodA are given beneath the nucleotide sequence beginning at bases 47, 289, and 834, respectively. The region designated "consensus" is the nod box sequence.

DETAILED DESCRIPTION

The terminology of this invention is briefly described as follows. "*Bradyrhizobium japonicum*" refers to a strain of Gram negative, soil bacteria which can nodulate soybean and a few other leguminous species, and fix nitrogen. A "recombinant DNA clone" is a genetic element (DNA polymer) which is capable of independent replication in bacteria. The clone is composed of a vector, containing the genetic determinants of replication and for selection (e.g., antibiotic resistance), and the insert DNA which is the DNA of interest, i.e. contains one or more genes. In the literature the term "recombinant DNA clone" is also used to describe bacteria containing the foregoing genetic element. This definition is not intended for purposes of the present specification. "Nod+" designates the phenotype of *B. japonicum* having the ability to nodulate leguminous plants. "Nod−" designates the phenotype of *B. japonicum* which does not have the ability to nodulate soybean. A "restriction enzyme" is an enzyme capable of cutting double-stranded DNA at a specific site determined by the DNA sequence. Two common restriction enzymes used in experiments with DNA from Rhizobium and Bradyrhizobium bacteria are Eco RI and Hind III. A "restriction enzyme DNA fragment" is a piece of DNA separated from the parent molecule by digestion with a restriction enzyme. "Oligodeoxyribonucleotide" refers, for purposes of this invention, to a relatively short series of nucleotides, e.g. less than 1000, in the form of an oligomer out of its natural environment, either alone or in combination with a vector or the like. "Complement" refers to the nucleotide sequence which would base pair with a given nucleotide sequence. All of these terms are well known in the art.

One aspect of the present invention relates to the isolation and identification of the nodABCD genes of *B. japonicum*. The ability of *B. japonicum* to establish a $N_2$-fixing symbiosis with leguminous plants is of great agricultural significance, especially with regard to the primary host plant, soybean, which is the second largest crop plant in the U.S. Soybean is also the largest leguminous crop worldwide. The nodABCD genes identified are essential for nodulation since mutations in these genes prevent or delay soybean nodulation.

Figure 1:
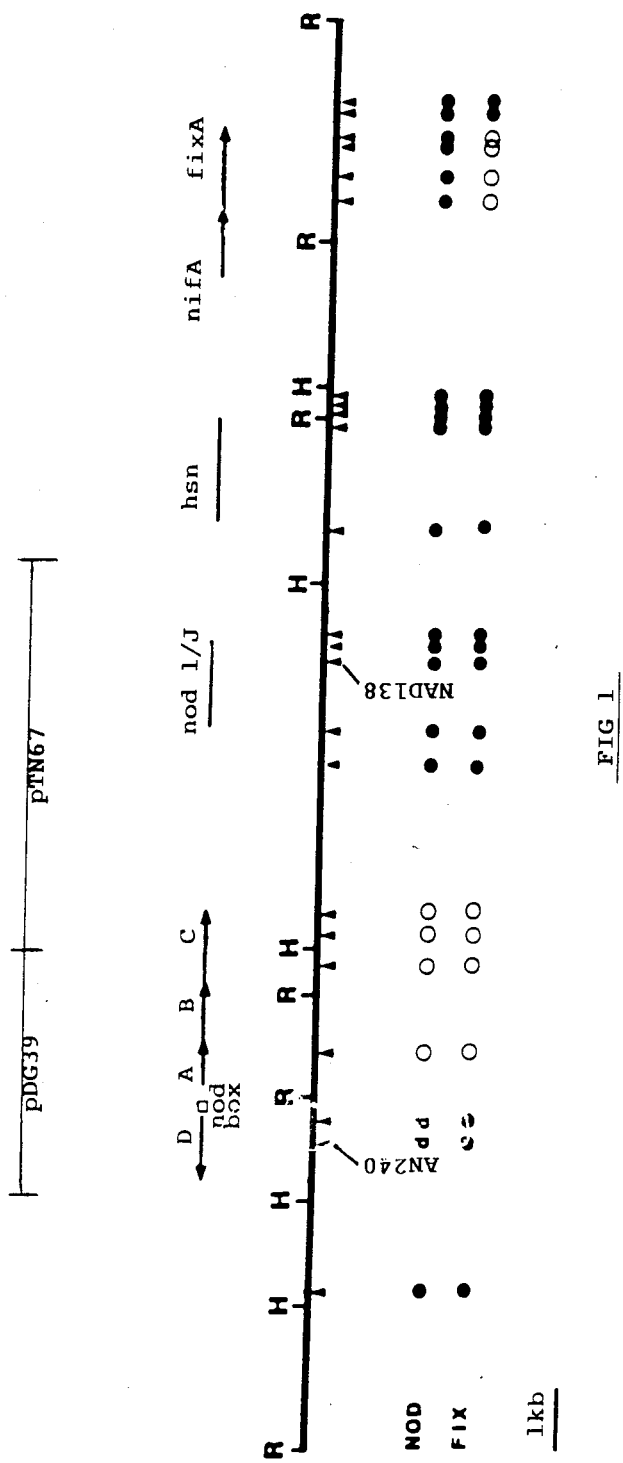
FIG. 1 is a diagram showing nodulation characteristics of *B. japonicum* Tn5 insertion mutants mapping within pRjUT10. Only a portion of pRjUT10 is shown. The fragments subcloned within pDG39 and pTN67 are indicated. Sites of insertions are indicated by triangles, and the different symbols underneath correspond to different Nod and Fix phenotypes resulting from tests on soybean plants. Wildtype (positive performance) is designated by darkened circles, negative performance by open circles, and delayed nodulation by the letter d. For restriction enzyme sites, EcoRI=R, HindIII=H.

FIG. 1 illustrates the positions of the nodABCD genes of the *B. japonicum* chromosome. The positions of these genes and the other regions identified in FIG. 1 are uniquely characterized by the restriction map of the chromosome at the involved region. The restriction map in this instance includes restriction sites for the enzymes EcoRI and HindIII. The map corresponds to the fragment sizes determined by Russell et al. for pRjUT10. The HindIII restriction map sequence is, from right to left, 3.3, 5.6, 3.9, 1.7, 2.3, 4.5, 4.6 and 4.3 kb, the first four of these fragments being indicated in FIG. 1. The EcoRI sequence shown in FIG. 1 is, from right to left, 3.8, 2.9, 9.4, 1.6 and 5.7 kb.

These genes may be manipulated using well established genetic engineering techniques in order to enhance the nodulating ability of *B. japonicum* strains or other rhizobia. In general, a rhizobia strain will be unable to effectively nodulate soybean unless all four of the nodA, nodB, nodC, and nodD genes of *B. japonicum* are present. A strain lacking one or more of these genes is termed NodA−, NodB−, etc., and more generally a strain lacking nodulation ability is termed simply Nod−. The nodIJ genes shown in FIG. 1 also affect nodulation.

This invention relates more specifically to recombinant DNA clones which contain the nodLABCDIJ genes of *B. japonicum*. The specific recombinant DNA clones referred to herein as pTN67 and pDG39, which contain 5.6 and 3.9 Kb HindIII restriction fragments, respectively. These HindIII fragments are contiguous on the *B. japonicum* chromosome. The gene regions identified on the above mentioned recombinant DNA clones specifically identified as nodulation genes are as follows:

pDG39: 3.9 Kb HindIII fragment containing nodDLAB and part of nodC; and pTN67: 5.6 Kb HindIII fragment containing part of nodC and nodIJ.

These clones may be used to restore nodulating ability to Nod- mutants of Bradyrhizobium or Rhizobium strains. Thus, these genes may be manipulated to enhance the nodulating ability of rhizobia. In addition, the regulatory DNA sequences of the nodABC gene transcript could potentially be fused to any gene of interest resulting in the ability to induce transcription only in the presence of suitable plant-produced chemicals, as described in detail hereafter.

Figure 2:
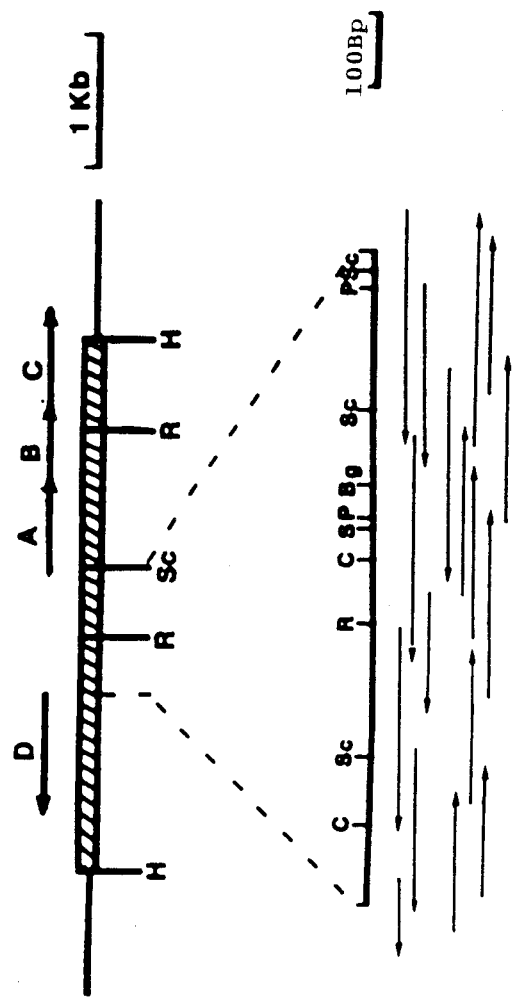
FIG. 2 is a partial restriction map of the promoter region of nodLABC. The arrowed figures describe the sequencing strategy. Arrows indicate direction and length of sequence.

The basic clones pTN67 and pDG39 may be used to prepare subclones containing one or more of the nodABCDIJL genes. Subclones of pTN67 and pDG39 may be readily created by known methods by means of restriction enzymes other than HindIII to further subdivide the fragment, such as the restriction enzymes noted above in connection with FIG. 2. Thus, a subclone could be readily developed from pDG39 containing only the nodD, nodL, the promoter region DNA, or combinations thereof. FIG. 2 shows a variety of restriction sites useful for preparing subclones containing portions of the nucleotide sequence given in FIG. 3.

The vector DNA utilized in the above clones or subclones could be either plasmid, cosmid, or bacteriophage. The vector DNA to which the nod gene regions are attached may be of a type capable of being introduced and maintained in B. japonicum In the specific clones referred to above, the vector DNA is pVK102 (Knauf et al, 1982, Plasmid 8:45-54.)

The Bradyrhizobium japonicum strain from which these regions are derived could be any strain containing the genes essential for successful nodulation of a leguminous host plant, particularly a soybean plant. The specific B. japonicum strain used for the purposes of the examples below was strain USDA 110 (See Kuykendall et al, 1976, Appl. Environ. Microbiol., 32:511-519.)

The leguminous host of B. japonicum strains created according to the invention having enhanced nodulation properties include varieties of soybean (Glycine max C. Merr.), cowpea (Vigna unguiculata), siratro (Macroptilium atropurpureum), and other suitable leguminous plants. The specific host used in the examples below was soybean, more specifically, soybean cultivar Essex.

According to the method of the invention, the genetically enhanced strains of B. japonicum will have enhanced nodulation properties for one or more host plants such as soybean, cowpea, and siratro. Specifically, the plant is innoculated with an inoculum comprising a particulate carrier such as peat and a strain of genetically enhanced bacteria according to the invention. In the resulting plants, the number of nodules per plant and/or the size of the nodules is increased as compared to plants innoculated with the original parent strain from which the genetically enhanced B. japonicum strain was derived.

The genes in the 5.6 and 3.9 Kb HindIII regions mentioned above were identified by:
(1) hybridization with previously identified genes from R. meliloti (Long et al, 1982, Nature 298:485) and R. leguminosarum (Downie . et al, 1983, Mol. Gen. Genet. 190:359),
(2) DNA sequencing,
(3) transposon Tn5 mutagenesis, and
(4) complementation of a NodD− mutant of R. meliloti.

A Nod− B. japonicum mutant may be converted to a Nod+ mutant according to the method of the invention. By definition the Nod− mutant is deficient, that is, lacks one or more required nod genes. Thus, using an appropriate recombinant DNA clone for each region, such as pDG39 or pTN67, the Nod− strain may be imparted with one or more of the nodABCDIJL functions and thereby have its nodulation ability enhanced (it becomes Nod+). The step of transferring the genes may be carried out by conventional genetic transfer techniques, such as triparental mating according to the method of Long et al, Nature, 1982, 298:485-488, utilizing plasmids such as pLAFR1 and pVK102. The desired strains are then obtained by selective culturing in the presence of an antibiotic to which strains containing the recombinant DNA are resistant. The surviving strains of Rhizobium or Bradyrhizobium have the nodulation gene(s) according to the invention incorporated therein.

Each of the foregoing clones is derived from the single chromosome of B. japonicum consisting of approximately 7,000 Kb. The techniques used to identify the common nodulation genes from B. japonicum strain I-110 and form the corresponding recombinant DNA clones are well known in the art and are not set forth in detail in the examples below other than by reference to publications describing the details of the techniques, the contents of which publications are hereby incorporated herein by reference.

The induction of the nodABC genes requires the presence of an active nodD gene product. The DNA region controlling nodABC transcription responds to host produced chemicals. These chemicals are flavones (flavone derivatives) such as luteolin for other species of rhizobia (See, e.g., Peters et al cited above) and similar compounds are also present in soybeans. In soybeans, the flavone derivative interacts with the nodD gene and the region adjoining it, which is designated the promoter region according to the present invention. The nodD gene likely acts as a positive effector on nodABC transcription in the presence of the flavone inducer. Due to the similarity between the nodABC genes of Rhizobium spp. and Bradyrhizobium species, these genes will be regulated in a similar fashion.

FIG. 3 shows the nucleotide sequence for the terminus of nodD and the entirety of the promoter region, the sequence between nodD and open reading frame 1 (ORF 1) which has been designated nodL according to the invention. The nod box sequence, designated "consensus" in FIG. 3, is an essential part of the promoter region, and may be the only part thereof actually needed, along with nodD, to induce nodABC transcription. Thus, the oligomer corresponding to the concensus sequence can be used in conjunction with the nodD sequence as a means of controlling gene expression in other organisms, e.g. other rhizobia. These oligomers can be transferred to foreign chromosomes by conventional genetic engineering techniques, whereon these sequences can be fused to any gene to control expression of such gene. The foreign gene in the position of nodLABC of the B. japonicum chromosome will be expressed (transcribed) only in the presence of the required soybean flavone.

A organism containing such controlled expression can be used to great advantage in any situation where the controlled gene is only desirably expressed in the presence of the host plant, or other source of the substance that triggers transcription. For example, according to the invention, a bacterial strain can be readily prepared which will contain, as the gene controlled by nodD and the promoter sequence, a gene encoding for a parasite toxin. The strain Bacillus thuringiensis produces a toxin for insect larvae. The toxin encoding genes of B. thuringiensis and other species have been characterized. See Aronson et al, *Microbiol. Rev.,* March 1986, pp 1–24, the entire contents of which are incorporated herein by reference. Using the gene for the BT toxin in place of nodABC in rhizobia, a symbiotic bacterial strain according to the invention may be prepared which will infect soybean roots and, in the presence of those roots, produce the BT toxin which will selectively protect the soybean plant from insect larvae.

This method has the advantage of causing the toxin to be produced only in the environment where it is needed. No toxin is produced if the bacteria is not in the presence of the designated plant, such as soybean. Rhizobia inoculum presently sold for soybean includes a carrier such a peat and one or more strains of bacteria destined to be brought in contact with the soybean plant roots. No toxin would be produced by the living bacteria in the product until the bacteria are in the presence of the soybean plant, eliminating possible problems with toxicity. In addition, many strains of rhizobia (Rhizobium and Bradyrhizobium) infect more than one plant species. Since the flavones for each plant species are generally unique, the toxin would not be produced if the strain were to infect the wrong crop.

The toxin gene may be transferred to the selected bacterial strain using known recombinant DNA techniques. See, for example, Vaeck et al, *Nature,* 1987, 328:33–37, the entire contents of which are incorporated herein by reference, describing transfer of BT toxin genes to the DNA of tobacco plants. The plants containing the toxin genes according to Vaeck et al. produced toxins which killed the insect larvae.

FIG. 3 describes several other useful nucleotide sequences. The sequence GATAAA is a Shine-Dalgarno (S-D) sequence for nodL. The oligomer GATAAAX, wherein X represents from about 6 to 12 of any of cytosine (C), guanine (G), adenine (A) or thymine (T), provides the point of alignment needed for transcription of nodL. Similarly, the sequence AAGAAGX acts as an S-D sequence for nodA. These oligomers are useful for the study and control of the genes they are associated with.

The role of nodL in nodulation is not clearly understood. However, due to its close relationship with nodABCD, manipulation of nodL, i.e. inserting it into or removing it from the bacterial chromosome, should give rise to changes in nodulation phenotype in rhizobia.

The following examples outline the identification of the nodDLABCIJ genes, evidence for the essential role of these genes in nodulation, and demonstrate the functionality of nodD.

EXAMPLE 1 Identification of the nodDLABCIJ genes

General Methods

Bacterial strains and plasmids used in this study are listed in Table 1 set forth below. *B. japonicum* cultures were grown in YS medium which contain 1 gram (gm) per liter yeast extract added to the previously described minimal salts/vitamin base of Bishop et al, 1976, *Plant Physiol.* 57:542–546, or in RDY medium containing, per liter: 5 gm gluconic acid, 1 gm glutamic acid, 1 gm yeast extract and mineral salts/vitamin base. *Escherichia coli* cultures were grown in LB medium (Maniatis et al, 1982, *Molecular cloning: A laboratory manual.* Cold Spring Harbor Laboratory, Cold Spring Harbor, NY) with the exception of JM101 which was grown in TYE (Sanger et al, 1977, *Proc. Natl. Acad. Sci. USA* 74:5463–5467.) *R. meliloti* was grown in TYA medium (Orosz et al, 1973, *Mol. Gen. Genet.* 125:341–350.)

TABLE 1

| Bacterial Strains, Plasmids, and Phages | |
|---|---|
| Bacterial Strain, Plasmid, or Phage (source) | Relevant Characteristics |
| Bacteria: | |
| *B. japonicum* USDA 110 (1) | Wild type, colony type I110 |
| *E. coli* DH-1 (2) | F-, recA1, endA1, gyrA96, thi-1, hsdR17, supE44, lambda- |
| *E. coli* HB101 (3) | F-, hsdS20, recA13, ara-14, proA2, lacY1, galK2, rpsL20, xyl-5, mtl-1, supE44, lambda- |
| *E. coli* DBCS31-1 | recA, trpE, lambda+ |
| *E. coli* JM101 (4) | (lac proA,B) supE, thi/F', traD36, proAB, lacIqZ M15 |
| *E. coli* EG47 (5) | hsdR, lac, gal, rpsL594 |
| *R. meliloti* AK631 | *R. meliloti* 41 |
| *R. meliloti* MG107 (6) | AK631 nodD::Tn5 |
| Plasmids: | |
| pRjUT10 (7) | pHC79 clone of *B. japonicum* |
| pRK2073 (8) | Trimethoprim$^r$, tra+ |
| pZB14 | pNM481::2.2 kb *R. meliloti* nodAB fragment |
| pZB15 | pBR329::3.2 kb EcoRI fragment nodIJ genes of *R. leguminosarum* |
| pCB507 (9) | pLAFR1 derivative carrying the hsn region of Rhizobium sp. strain MPIK3030 |
| pDG39 | pVK102 (26) derivative carrying the 3.9 HindIII fragment of *B. japonicum* 110 homologous to *R. meliloti* nodD |
| pIJ1089 (10) | *R. leguminosarum* nod and fix genes cloned as a 30 Kb fragment in pLAFR1 |
| pBR329 (11) | Amp$^r$ Tet$^r$ Cm$^r$ |
| Phages: | |
| Tn5 | Km$^r$ |
| P1 Tn5 (12) | Km$^r$ |
| P1 Tn5 lac | Km$^r$ |
| P1 clr100 cm (5) | Cm$^r$ |
| fFR nodC | M13 mp8::0.7 kb nodC fragment of *R. meliloti* |
| fMG nodD | M13 mp18::275 bp nodD fragment of *R. meliloti* |
| fBH hsnA | M13 mp18::0.5 kb hsnA fragment of *R. meliloti* |
| fBH hsnB | M13 mp18::0.5 kb hsnB fragment of *R. meliloti* |
| fBH hsnC | M13 mp18::1.6 kb hsnC fragment of *R. meliloti* |
| fFR hsnD | M13 mp18::320 bp hsnD |

Sources noted in Table 1:
(1) Kuykendall et al, 1976, Appl. Environ. Microbiol. 32:511–519
(2) Low, B. 1968. Proc. Natl. Acad. Sci. USA 60:160–166.
(3) Bolivar, F. 1978. Gene 4:121–136.
(4) Messing et al, 1981. Nucl. Acids Res. 9:309–321.
(5) Goldberg et al, 1974. J. Bacteriol. 118:810–814.
(6) Gottfert et al, 1986. J. Mol. Biol. 191:411–20.
(7) Russell et al, 1985. J. Bacteriol. 164:1301–1308.
(8) Leong et al, 1982. J. Biol. Chem. 257:8724–8730.
(9) Bachem et al, 1986. Mol. Gen. Genet. 203:42–48.
(10) Downie et al, 1983. EMBO J 2:947–952.
(11) Boyer et al, 1976. J. Mol. Biol. 41:459–465.
(12) Quinto, et al, 1984. Appl. Environ. Microbiol. 47:436–438.

DNA isolation

Plasmid DNA was isolated on a large scale as described by Davis et al, or on a small scale essentially as described by Maniatis et al. Both methods are described in *Advanced Bacterial Genetics,* Cold Spring Harbor Laboratory, Cold Spring Harbor, NY, 1980.

Cloning procedures

Cosmid pIJ1089 carrying the nodulation genes *R. leguminosarum* (Downie et al, EMBO J. 2:974) was digested with EcoRI and a fragment of 3.3 kb containing the nodIJ genes (Downie et al, 1983, *Mol. Gen.*

Genet. 190:359) was isolated from an agarose gel by electroelution (Maniatis et al noted above). The vector plasmid pBR329 (Boyer et al, 1969, J. Mol Biol. 41:459) was linearized by EcoRI and ligated to the isolated fragment and subsequently transformed into the E. coli strain DH1, selecting for tetracycline resistance colonies on LB Tet (20 µg/ml) medium. Tetracycline resistant, chloramphenicol sensitive colonies were isolated by replica plating onto LB Tet and LB Tet Cm (20 µg/ml and 30 µg/ml respectively) plates. The resulting plasmid from one such colony was designated pZB15 and was used as the source of nodIJ DNA hybridization probe in further experiments.

Likewise the cosmid pRjUT1O containing the common nodulation genes of B. japonicum (Russell et al, 1985, J. Bacteriol. 164:1301-1038) was digested with HindIII and fragments of 3.9 and 5.6 kb containing homology to the R. meliloti nodD and nodC gene, respectively, were isolated from an agarose gel by electroelution (Maniatis et al noted above). The vector plasmid pVK102 (Knauf et al, 1982, Plasmid 8:45-54) was linearized by HindIII and ligated to the isolated fragment and subsequently transformed into the E. coli strain DH1 selecting for tetracycline resistant colonies on LB Tet (20 µg/ml) medium. Tetracycline resistant, kanamycin sensitive colonies were isolated by replica plating onto LB Tet and LB Km (20 µg/ml and 25 µg/ml respectively) plates. The resulting plasmids from two such colonies were designated pDG39 (containing the 3.9 Kb HindIII fragment) and pTN67 (containing the 5.6 Kb HindIII fragment.)

Blotting and hybridization

DNA restriction fragments were transferred to nitrocellulose filters as described in Southern, 1975, J. Mol. Biol. 98:503-517. Internal fragments from the intra-nod and hsn genes of R. meliloti cloned into the phage M13 were labeled as described by Sanger et al, 1977, ibid) using Klenow enzyme, 32P-dCTP and a 17-mer primer DNA (Bethesda Research Laboratories, Inc.) except for hsnD where a reverse primer (BioLabs Inc.) was used. The DNA fragments containing the nodIJ genes of R. leguminosarum and the hsn genes of R. sp. MPIK3030 were reisolated from agarose gels (Maniatis et al noted above) and labeled by the random primer method of Feinberg and Vogelstein, 1982, Anal. Biochem. 132:6-13. From both methods specific activities of $1 \times 10^8$ cpm/µg were obtained. Hybridizations were carried out in 50% formamide buffer at 37° C. according to Kondorosi et al, 1982, Mol. Gen. Genet. 182:435-439. Filters were washed at 37° C. twice for 1 hour in 2X SSC (1X SSC contains 15 mM sodium citrate and 150 mM NaCl [pH 7.0]) and 0.1% SDS and twice for 1 hour in 2X SSC. Exposure of X-ray film was as described by Maniatis et al.

Nod-Box DNA from R. meliloti, a 25-mer oligodeoxyribonucleotide d(ATAAAAACAATCGATTTTAC-CAATC), was used for hybridization essentially as described previously by Rostas et al, 1985, Proc. Natl. Acad. Sci. USA 83:1757-1761.

Enzymes and isotopes

DNA restriction endonucleases and modifying enzymes were purchased from New England Biolabs, Boehringer Mannheim or Bethesda Research Laboratories and was used according to the manufacturers recommendations. Radioactive nucleotides were purchased from New England Nuclear.

DNA sequencing

DNA sequences were determined by the dideoxy chain termination method as described (Amersham Corp. M13 Cloning and Sequencing Handbook, Arlington Hts, Ill. 1983.) A nested set of deletions of the cloned fragments in mp18 and mp19 was generated by the method of Henikoff, 1984, Gene 28:351-359.

Site directed Tn5 mutagenesis

Tn5 mutagenesis was performed in E. coli strain HMS174 according to de Bruijn and Lupski, Gene 27:131) or in E. coli strain EG47 according to Quinto and Bender, 1984, Appl. Environ. Microbiol. 47:436. Mutated fragments were conjugated from E. coli to B. japonicum:USDA 110 by the triparental mating system described by Ditta et al, 1980, Proc. Natl. Acad. Sci. USA 77:7347. The Tn5 mutated fragments were marker exchanged for the corresponding wild-type DNA by double reciprocal crossover technique of Ruvkun and Ausubel, 1981, Nature 289:85. The occurrence of the reciprocal recombination event was confirmed in most cases by hybridizing EcoRI digests of total DNA isolated from the mutants with a Tn5 probe, pSUP1011 (Simon, et al, 1983, Biotechnol. 1:784.) The hybridization data confirmed the location of the Tn5 insertions mapped on pRjUT1O.

Plant tests

Seeds (Glycine max cv. Essex) were surface sterilized and germinated as described in Wacek et al, 1976, Crop. Sci. 15:519). Seedlings (2 days old) were planted in 35 ml serum vials containing sterile vermiculite saturated with sterile plant nutrient solution (PNS) supplemented with 1% sucrose and covered with sterile 18 oz. Whirlpak bags (Nasco). Plants were maintained for 21 days at 26° C. in a growth room supplying 320 $Em^{-2}S^{-1}$ with a 14 hour photoperiod. Nitrogen fixation activity was detected by the acetylene reduction assay using a Shimadzu GC-8A gas chromatograph equipped with a 6 feet Poropak R column. The detector was maintained at a temperature of 100° C. and the column at 75° C. Plant roots were examined for nodules.

For delayed nodulation assays, seedlings (Glycine max) were sprouted as before then grown three to a pack in clear plastic pouches (dispo Seed Pack, Northrup King Seed Co.) as described in Halverson et al, 1985, Plant Physiol. 77:621. Alfalfa (Medicago sativa) plant assays were carried out in test-tubes on nitrogen free medium as described in Kondorosi et al, 1977, Mol. Gen. Genet. 151:221.

RESULTS

Identification of Symbiotic Regions

The nodABCD genes of R. meliloti were cloned by the method of Long et al, 1982, Nature (London) 298:485-488, and located on a 8.5 Kb EcoRI fragment. We utilized this 8.5 Kb fragment as a hybridization probe to a genomic library of B. japonicum USDA 110. A single clone (pRjUT1O) was obtained that showed homology to the R. meliloti nod gene fragment as described by Russell et al, discussed above. In order to identify and delimit symbiotic genes, clone pRjUT1O was subjected to site-directed Tn5 mutagenesis. The resulting mutants are shown in FIG. 1. The position of the Tn5 insertion points were checked and mapped by restriction endonuclease digestions. In the case of insertions in the nodABCD region, placement of the insertions was aided by restriction enzyme sites obtained from the DNA sequence. The mutated DNA was subsequently homogenotized into *B. japonicum* USDA 110 and nodulation and nitrogen fixation assays were performed as described in materials and methods.

The following three mutant classes were obtained on soybean (*Glycine max* cv. Essex) seedlings:
(1) Delayed Nod+ (Letter d in FIG. 1) two to four days delayed in nodulation and reduced efficiency of nodulation; normal nodule morphology and nitrogen fixation;
(2) Nod− (open circles FIG. 1) phenotype with less than 2% of the plants assayed showing some abnormal nodule-like structures after 21-28 days; and
(3) Nod+, Fix−(closed circles, open circles, respectively, FIG. 1).

No significant delay in nodulation compared to the wildtype strain. However these mutants could not fix atmospheric nitrogen. This Fix− region has been shown previously to have homology to the fixA and nifA genes of *R. meliloti* (Lamb et al, 1986, *Mol. Gen. Genet.* 102:512).

Hybridization of nod regions

To further characterize the nodulation regions identified and to locate other nodulation regions previously identified in other Rhizobium strains, specific nod DNA probes from *R. meliloti* and *R. leguminosarum* were hybridized to pRjUT10. The nodABC and nodD genes of *R. meliloti* hybridized to two HindIII fragments of 5.6 and 3.9 kb, respectively. The nodAB region was localized to the 3.9 kb HindIII fragment and was wholly contained within the 1.6 kb EcoRI fragment (FIG. 1). The nodC specific homology was predominantly to the left end of the 9.4 kb EcoRI fragment since it also hybridized to the 5.6 kb HindIII fragment.

The nodD specific homology was located on a 5.8 kb EcoRI fragment and a 3.9 kb HindIII fragment and was found to be completely within a 1.8 kb EcoRI-HindIII fragment at the right end of the 5.8 kb EcoRI fragment.

Within the 9.4 kb EcoRI fragment and the 5.6 kb HindIII fragment, a region hybridized to the *R. leguminosarum* nodIJ probe. In order to localize the nodIJ homologous region, nine pRjUT10 cosmid clones containing Tn5 insertions within the 5.6 kb HindIII fragment were restricted with HindIII and probed with the nodIJ fragment (data not shown). The nodIJ homologous region was localized to a 1.5 kb region approximately 0.5 kb from the right end of the 5.6 kb HindIII fragment or about 2.5 kb from the end of the nodC gene (FIG. 1). The Tn5 mutants in this region showed wildtype nodulation and nitrogen fixation phenotypes, with at most a one day delay in nodulation.

Identification of the nodL gene

In order to identify possible DNA sequences involved in the regulation of the nodD or nodABC transcripts, the 1.7 Kb EcoRI fragment wholly contained within the 3.9 Kb HindIII fragment of pDG39 was cloned into M13 bacteriophage vectors and sequenced as described in methods. The region lying between the nodA and nodD genes was sequenced completely from both DNA strands. This sequence reveals the presence of an unsuspected protein coding region 5' of the nodA gene. This protein coding region is 420 bases in length and in an analogous position to the nodK gene identified in *B. parasponiae* (Scott, K. F. 1986. *Nucl. Acids Res.* 14:2905-2929). Although of similar size and location as the *B. parasponiae* nodK gene, the protein coding region identified in *B. japonicum* has only 30% overall homology to the nodK gene. For this reason, the identified protein coding region is a novel protein and has been named the nodL gene. The DNA sequence and predicted amino acid sequence of nodL is shown in FIG. 3.

EXAMPLE 2: Functionality of the nodD gene and regulatory sequences.

General Methods

The same methods as described above for Example 1 were employed.

RESULTS

Identification of DNA regulatory sequences

As noted in the foregoing publications, the nodABC genes of Rhizobium species have been shown to be induced only in the presence of the plant. Plant produced phenolic compounds (i.e., flavones, flavonones) have been shown to be required for nodABC induction. A functional nodD gene product is required for induction to take place. NodD interacts with the plant inducer and binds to the nodABC gene promoter to stimulate transcription. A DNA sequence 5' to the nodABC gene region has been shown to be conserved among various Rhizobium and Bradyrhizobium strains. Deletion of this sequence, termed the Nod Box, results in an inability to induce the nodABC transcript.

We utilized a 25 bp highly conserved sequence from the *R. meliloti* Nod Box sequence as a probe to *B. japonicum* DNA. This probe located the homologous DNA region within the 3.9 Kb HindIII fragment contained in pDG39. This identified Nod Box sequence is contained within the DNA sequenced and is shown in FIG. 3. By analogy to the studies of Rhizobium species, this sequence is necessary for the regulation of the nodLABC gene transcript.

Complementation of NodD

The nodD gene is of special importance since it has been suggested to encode a regulatory protein. Since hybridization data cannot determine a region's functionality, additional experiments were done. Clone pDG39 containing the 3.9 kb HindIII fragment showing homology to the *R. meliloti* nodD gene was used to complement a nodD− mutant of *R. meliloti*. Whereas the wildtype strain of *R. meliloti*, strain AK631, was able to nodulate alfalfa in 15 days, the NodD− mutant, strain MG107, was delayed approximately 9 days. However, the NodD− mutant strain containing the *B. japonicum* 3.9 kb HindIII fragment was able to efficiently nodulate alfalfa with only a slight (2 day) delay. These data clearly indicate that a functional nodD gene is present on the 3.9 kb HindIII fragment. Since the nodD gene in *R. meliloti* has been shown to play an essential role in the regulation of nodABC transcription, these results strongly support the conclusion that the nodD gene of *B. japonicum* is involved in nodLABC regulation.

It will be understood that the above description is of preferred exemplary embodiments of the invention, and that the invention is not limited to the specific forms shown. Modifications may be made in the compositions and methods according to the invention without departing from the scope of the invention as described in the appended claims.

We claim:

1. An oligodeoxyribonucleotide consisting essentially of the sequence:

5'-ATGCAGATATCATCCGTTTCCATATTT-CAGGTTTACCCGCGTAC AATTGAGGGCGCGTTCAGCCTCATT-CTAGTGTCGAAGAATAG AGGCAGACG-CAGGTTGCGGATGCCAAGAATT-CCAGGCGCCGTTC CAAATGGCTCGCCTGTCCAGT-GCATGTGGGCGTGTCGAAGA TGTA-TAAAAGCCAGTGTGATCT-GATGCCGCTCCGATGCGCCATC GAT-GAGGCTTGCGCGCCGATGGCCGGCCCT-CAGACGTCAAAGCGC CGGAGGCATG-CGACTGCAGGCACAAAAGCTCGCTGGT-GCAGACA GGTTCTGCTAGC-CCAACCGCCTCGTCGGCAGCTTCCGACT-TATCG TGAGCGCGGCATCAACCGCAC-GAGGGTGCAATCAAGCGATCGCT CCGTCGCGCAAAGGCCAGCGCGCGAG-TAG-3' wherein A represents adenine, T represents thymine, C represents cytosine, and G represents guanine, and a complement thereof, having activity as a nodL gene sequence in *Bradyrhizobium japonicum*.

2. A recombinant DNA clone, consisting essentially of a vector and the oligodeoxyribonucleotide of claim 1.

3. A strain of *B. japonicum* prepared by complementation of a nodL− *B. japonicum* strain with the